United States Patent [19]
Haines

[11] Patent Number: 5,929,062
[45] Date of Patent: Jul. 27, 1999

[54] OXYSTEROL INHIBITION OF DIETARY CHOLESTEROL UPTAKE

[75] Inventor: Milton Haines, London, Canada

[73] Assignee: University of Western Ontario, London, Canada

[21] Appl. No.: 08/878,731

[22] Filed: Jun. 19, 1997

[51] Int. Cl.$^6$ ...................................................... A61K 31/56
[52] U.S. Cl. ........................................... 514/182; 514/824
[58] Field of Search ...................................... 514/182, 824

[56] References Cited

U.S. PATENT DOCUMENTS

| | | | |
|---|---|---|---|
| 5,244,887 | 9/1993 | Straub | 514/182 |
| 5,502,045 | 3/1996 | Miettinen et al. | 514/182 |

OTHER PUBLICATIONS

Folch et al., "A Simple Method for the Isolation and Purification of Total Lipides from Animal Tissues", *J. Biol. Chem.*, 1957, 226, 497–509.

Kelley et al., "Effect of Pectin, Gum Arabic and Agar on Cholesterol Absorption, Synthesis, and Turnover in Rats", *J. Nutrition*, 1978, 108, 630–639.

CA 89:71635, Erickson et al, 1978.

CA 89:186088, Kitame et al, 1978.

*Primary Examiner*—Kimberly Jordan
*Attorney, Agent, or Firm*—Woodcock Washburn Kurtz MacKiewicz & Norris LLP

[57] ABSTRACT

A composition useful to inhibit cholesterol absorption from the diet is provided. The composition comprises a pharmaceutically acceptable combination of one or more oxysterols and a suitable carrier. The present oxysterol composition can be used therapeutically, prescribed to individuals who are required to reduce cholesterol intake. Alternatively, the composition can used as a dietary supplement by any individual desiring to moderate cholesterol intake.

24 Claims, 4 Drawing Sheets

OXYSTEROL INHIBITION OF DIETARY CHOLESTEROL UPTAKE

FIELD OF THE INVENTION

The present invention relates to cholesterol-lowering compositions. More particularly, the present invention relates to a novel oxysterol composition useful to inhibit the absorption of dietary cholesterol.

BACKGROUND OF THE INVENTION

Atherosclerosis is a disease that involves the deposit of lipids, with an especially high concentration of cholesterol, on the walls of the large arteries. Often, calcium precipitates the lipid build-up to form calcified plaques which leads to arteriosclerosis, more commonly known as "hardening of the arteries". The seriousness of this disease is evident from the fact that it is the cause of death for almost half of the human population. Although the cause of atherosclerosis can be attributed to a number of factors, it is clear that a diet which is high in cholesterol substantially increases one's chances of developing atherosclerosis.

In an attempt to prevent atherosclerosis and associated heart disease, cholesterol-lowering drugs have been developed and are currently widely prescribed. The drugs at the forefront of this market incorporate compounds belonging to the "statin" family. These include pravastatin (Bristol-Myers Squibb Company), simvastatin (Merck and Company) and cerivastatin (the Bayer Group). This group of compounds are potent inhibitors of cholesterol synthesis and function by inhibiting HMG CoA reductase, an enzyme that catalyzes the synthesis of a precursor to cholesterol. Not only may such drugs have serious side effects, they do not function in any way to control the intake of cholesterol through diet. They function only to prevent the internal synthesis of cholesterol synthesized primarily by the liver.

Since the 1950's, plant sterols such as sitosterol, stigmasterol and campesterol have been added to patients' diets to treat hypercholesterolemia, a condition of elevated blood cholesterol levels. U.S. Pat. No. 5,244,887, issued to Straub Sep. 14, 1993, discloses a method for making a food additive composition useful to reduce cholesterol absorption from foods and beverages. The composition contains stanols, derivatized forms of sterols, and specifically, contains a stanol selected from the group consisting of clionastanol, 22,23 dihydrobrassicastanol, campestanol and sitostanol, admixed with an edible solubilizing agent, an antioxidant and a dispersant.

U.S. Pat. No. 5,502,045, issued to Raision Tehtaat Oy A B Mar. 26, 1996, teaches the use of a beta-sitostanol fafty acid ester that is also useful to reduce serum levels of cholesterol in patients by inhibiting cholesterol absorption. The active sitostanol ester is prepared from naturally occurring plant sterols derived from green plants and trees, particularly pine trees. At present, however, it is difficult to acquire the essential naturally occurring ingredients in quantities large enough to satisfy the market demand and this poses a significant drawback to products of this nature. Moreover, a further disadvantage of these plant sterols, and particularly those derived from pine trees, is the presence of an unpleasant "pine cone" taste in edible products incorporating a cholesterol-reducing sitostanol ester.

Due to the prevalence of coronary disease in our society, there remains a need to develop novel treatments which overcome the disadvantages of those presently on the market. Of particular interest are products which are therapeutically useful at the nutritional level so as to minimize the uptake of cholesterol and prevent the development of heart disease or conditions leading to it. It is an object of the present invention to provide such a preventative therapy, particularly to those at high risk of coronary heart disease.

SUMMARY OF THE INVENTION

It has now been discovered that oxysterols, which arise from the oxidation of cholesterol, have an inhibitory effect on the absorption of dietary cholesterol by the body. Such a composition has the potential to benefit a large proportion of the population. Not only are oxysterol compositions useful for that segment of the population already afflicted with heart disease or those at risk of developing heart disease, it can also be used by low risk individuals to maintain serum cholesterol at an acceptable level, particularly individuals inclined to indulge in a high fat diet.

Accordingly, in one aspect, the present invention provides a cholesterol-lowering composition that reduces absorption of dietary cholesterol by the body of a mammal, said composition comprising a pharmaceutically acceptable combination of one or more oxysterols and at least one carrier.

In another aspect, the present invention provides a method of reducing dietary cholesterol absorption by the body of a mammal comprising the step of administering to said mammal a therapeutically effective amount of a pharmaceutically acceptable oxysterol composition.

A yet another aspect of the present invention, a dietary supplement effective to reduce the absorption of dietary cholesterol in a mammal, said supplement comprising a pharmaceutically acceptable combination of one or more oxysterols with at least one carrier.

In a further aspect of the present invention, an article of manufacture is provided comprising packaging material and a pharmaceutical composition contained within said packaging material, wherein said pharmaceutical composition is therapeutically effective to reduce absorption of dietary cholesterol into the body of a mammal, and wherein the packaging material comprises a label which indicates that the composition can be used to reduce bodily absorption of dietary cholesterol, said composition comprising a pharmaceutically acceptable combination of one or more oxysterols and at least one carrier.

Embodiments of the present invention are described in greater detail with reference to the accompanying drawings in which:

DETAILED DESCRIPTION OF THE INVENTION

Figure 1:
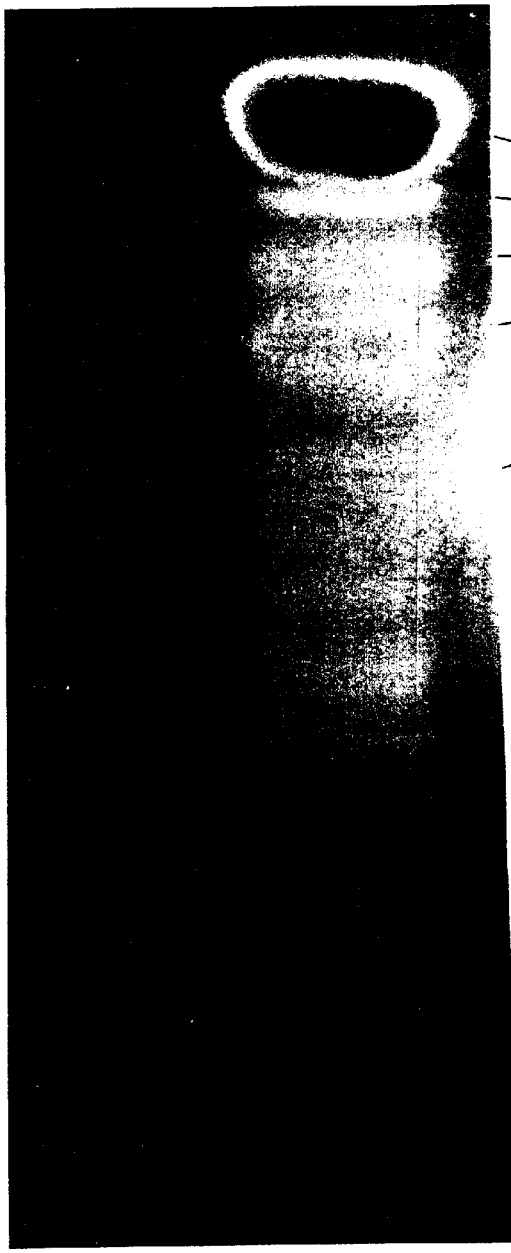
FIG. 1 illustrates the fractionation of oxidized cholesterol obtained by thin layer chromatography.

The present invention provides a pharmaceutically acceptable oxysterol composition which is effective to reduce the absorption of dietary cholesterol into the body of a mammal, including both human and non-human mammals. The term "oxysterol" as it is used herein with respect to a pharmaceutical composition is meant to encompass one or more forms of oxidized cholesterol which are either independently or collectively active to reduce dietary cholesterol absorption by the body. Moreover, the term "pharmaceutically acceptable" refers to an oxysterol composition acceptable for use in the pharmaceutical and veterinary arts, which is not toxic or otherwise unacceptable.

Oxysterols that may be used to form a pharmaceutically acceptable composition in accordance with the present invention include oxysterols that are more polar than cholesterol itself such as cholesterol-7-alpha-hydroperoxide; cholesterol-7-beta-hydroperoxide; cholest-5-ene-3-beta-7-alpha-diol; cholest-5-ene-3-beta-7-beta-diol; 3-beta-hydroxycholest-5-ene-7-one; 5,6-alpha-epoxy-5-alpha-cholestan-3-beta-ol; 5,6-beta-epoxy-5-alpha-cholestan-3-beta-ol; 5-alpha-cholestane-3-beta-5,6-beta-triol; cholest-5-en-3-one; cholest-4-en-3-one; 6-alpha-hydroperoxycholest-4-en-3-one; 6-beta-hydroperoxycholest-4-en-3-one; 6-alpha-hydroxycholest-4-en-3-one; 6-beta-hydroxycholest-4-en-3-one; cholest-4-ene-3,6-dione; 5-alpha-cholestane-3,6-dione; (20S)-cholest-5-ene-3-beta,20-diol; cholest-5-ene-3-beta, 25-diol; cholest-5-ene-3-beta, 26-diol; and 3-beta-hydroxycholest-5-en-24-one. Preferably the present composition includes one or more of the oxysterols selected from the group consisting of 25-hydroxy cholesterol (cholest-5-ene-3-beta, 25-diol), 20-hydroxy cholesterol ((20S)-cholest-5-ene-3-beta, 20-diol), 7-hydroxy cholesterol (cholest-5-ene-3-beta-7-beta-diol and cholest-5-ene-3-beta-7-alpha-diol isomers) and 5,6-cholestan epoxide (5,6-alpha-epoxy-5-alpha-cholestan-3-beta-ol and 5,6-beta-epoxy-5-alpha-cholestan-3-beta-ol isomers).

Such oxysterols are prepared by oxidizing cholesterol. Briefly, cholesterol is heated in the presence of oxygen to render a mixture of various oxysterols. In order to obtain the desired oxysterol(s), separation methods well-known in the art, such as column chromatography, can be used to separate the mixture of oxysterols into fractions containing individual oxysterols. The desired oxysterol fractions can then be selected for further purification by any of the standard approaches, for example reversed-phase high-pressure liquid chromatography (RP-HPLC), ion exchange chromatography and electrophoresis, to achieve oxysterol compounds of a suitable purity, i.e. a purity that satisfies the standards set by the various agencies which govern pharmaceutical products. It will be appreciated that strict standards of purity may not be required for use of the present compounds and compositions in the veterinary field.

According to one aspect of the present, a cholesterol-lowering composition is provided comprising a pharmaceutically acceptable combination of oxysterol and at least one carrier. Pharmaceutically acceptable carriers for inclusion into the present compositions include carriers most suitable for combination with lipid-based drugs such as diluents, excipients and the like which enhance its oral administration. Suitable such carriers include, but are not limited to, sugars, starches, cellulose and derivatives thereof, wetting agents, lubricants such as sodium lauryl sulfate, stabilizers, tabletting agents, anti-oxidants, preservatives, coloring agents and flavoring agents. Reference may be made to "Remington's Pharmaceutical Sciences", 17th Ed., Mack Publishing Company, Easton, Pa., 1985, for other carriers that would be suitable for combination with the present oxysterol(s) to render an orally ingestible composition. As will be appreciated, the pharmaceutical carriers used to prepare compositions in accordance with the present invention will depend on the administrable form to be used.

According to one embodiment of the invention, the present composition is formulated for oral administration. Oral dosage forms formulated in accordance with standard pharmaceutical practise, may be employed. Capsules are a particularly useful vehicle for administering the present composition due to the characteristic oily nature of oxysterols. The composition may also be formulated into an oily preparation for direct addition to foods.

The present composition can be prescribed for therapeutic use by individuals required to minimize cholesterol uptake. Individuals who are hypercholesteremic, individuals who have previously suffered from some form of heart disease or individuals at high risk of developing heart disease belong in this category. The oxysterol composition is taken on a regular basis at mealtime to prevent absorption of cholesterol from the diet.

Alternatively, the oxysterol composition can be used as a dietary supplement by any individual, and particularly individuals who regularly consume cholesterol-rich foods, in order to prevent hypercholesterolemia and ultimately, heart disease. In this case, the composition is taken preferably when cholesterol-rich foods are consumed, either independently in an appropriate oral dosage form, or combined directly with a food product in the form of an oily preparation as described above. In the latter case, the preparation is advantageously added to food products rich in cholesterol, or products that will be consumed with cholesterol-rich foods. For example, the preparation can be added to cooking oils, marinades, sauces, dairy products, beverages and additives that could suitably be combined with an oily preparation that is typically used in the preparation of foods high in cholesterol including meats, desserts and eggs.

In another of its aspects, a method of reducing dietary cholesterol absorption is provided. The method comprises administration of a "therapeutically effective amount" of the present oxysterol composition to a mammal, including both human and non-human mammals which may require treatment. By "therapeutically effective amount" is meant an amount of the composition indicated to reduce absorption of cholesterol while not exceeding an amount which may cause significant adverse effects. In this regard, precise dosage sizes appropriate to reduce cholesterol absorption can readily be established in appropriately controlled trials. It is anticipated that an effective treatment regimen will be the administration of an oxysterol dosage in the range of 100–1000 mg (0.1–1 g) per day.

A further aspect of the present invention provides an article of manufacture which includes packaging material contained within which is a pharmaceutically acceptable oxysterol composition that is therapeutically effective to reduce absorption of dietary cholesterol. The packaging material comprises a label which indicates that the composition can be used to reduce absorption of dietary cholesterol.

EXAMPLES

Example 1

The preparation of oxysterols

Oxysterols used in the present experiments were prepared by three methods.

A first oxysterol composition resulted from naturally-aged cholesterol, pure cholesterol (obtained from Fisher Scientific) which was left in a closed bottle at room temperature for 15 years.

A second oxysterol composition was prepared using low temperature heat. In this method, 100 g. of pure cholesterol (Sigma Chemical Co., St. Louis, Mo.) was heated on a glass tray in an electric oven at 65° C. The heating was continued for about 8–10 weeks to obtain a 50% oxidation of cholesterol to oxysterol.

A third oxysterol composition was prepared using high temperature heat. In this method, 100 g. of pure cholesterol was heated in an electric oven at 150° C. for 11.5 hrs. to obtain a composition of about 28–29% oxysterols.

The oxidized cholesterol mixtures were applied to silicic acid columns (50 mm×250 mm, Silica Gel G, 10–40 µm, Sigma Chemical Co., St. Louis, Mo.) dissolved in 30 ml chloroform. They were eluted with 200 ml of n-hexane/diethyl ether (9:1, v/v), then 200 ml of n-hexane/diethyl ether (1:1, v/v), 600 ml of diethyl ether and finally 600 ml of methanol. Aliquots of the polar fractions eluted with methanol were dried on a rotary evaporator in vacuo. Thin layer chromatography (TLC) analysis showed that the preparations consisted of more than 95% oxysterols and only traces of cholesterol. After weighing, the dried oxysterols were dissolved in 30–40 ml of absolute ethanol and kept tightly stoppered at −20° C.

FIG. 1 illustrates the distribution of oxysterols and cholesterol in a mixture oxidized as set out above. Fraction I, the polar fraction, contained oxysterols migrating between the origin and cholesterol. Fraction II contained cholesterol itself. Fraction III (not shown) contained some minor components migrating between cholesterol and the solvent front. The number of separated bands in each fraction depended on the method of oxidizing cholesterol. Naturally-aged cholesterol and cholesterol heated at 65° C. were very similar in chemical composition. They were usually resolved into 14–16 different oxysterol bands, most of them located in fraction 1, with prominent fraction II and minor fraction III. Oxysterols prepared by heating of cholesterol at 150° C. contained 30–40 different bands located in all three fractions.

The crude mixture of oxysterols is then subjected to chemical fractionation in order to purify separate and purify individual oxysterols. This involves application of the crude mixture to a silicic acid column and separation of the polar fraction (fraction 1 described above). The polar fraction will then be subjected to a gradient separation using a solvent of continuously increasing polarity, for example a methanol/chloroform solvent of increasing methanol content, thereby sequentially eluting individual oxysterols from the column. Each oxysterol will be collected and concentrated for use.

Example 2

In vivo Feeding Studies

Male Wistar rats, 200–250 g (Charles River Laboratories, Wilmington, Mass.) were individually housed in metal screen-floored cages under controlled illumination (0800–2000) and were allowed unrestricted access to food and water. Food intakes and body weights were monitored daily.

Groups of rats (four to six animals in each group), were fed one of the following diets:

i) basal diet supplemented with 1.5% cholesterol ii) basal diet supplemented with 2% oxidized cholesterol, either naturally-aged or generated by heating of cholesterol at 65° C. or at 150° C.;

iii) control or base line feeding consisted of basal (cholesterol-free) diet.

The granular basal diet was semisynthetic, nutritionally complete and cholesterol free. It had the following composition by weight: protein, 20%; carbohydrate, 64%; and fat, 10%. The remainder consisted of vitamins including 0.5% choline chloride, minerals and salts. The diets supplemented with i) cholesterol (1.5 g per 100 g diet) or ii) oxidized cholesterol (2.0 g per 100 g diet containing 1.5 g cholesterol and 0.5 g of oxysterol mixture) were prepared as follows. The cholesterol or oxidized cholesterol was dissolved in a minimum volume of absolute ethanol with slight warming. This was slowly added to the granular diet with constant mixing in an electric food mixer (Braun). The diet was then spread over a flat surface and the ethanol was allowed to completely evaporate over at least 4 days.

The experiment was conducted for 8 days. Total feces were collected daily. At the end of each experimental period (2, 4, 6, and 8 days) the rats were anesthetized with diethyl ether and exsanguinated by aortic puncture. The livers were excised, weighed and prepared for lipid assay. The total lipids of feces, liver and lymph were extracted by the method of Folch, Lees and Stanley (Journal of Biological Chemistry, (1957), vol. 226, page 497) with at least 2-volumes of chloroform/methanol (2:1, v/v). The separated chloroform extracts were concentrated under an air stream or in vacuo and were made to specific volumes (usually 6 ml) in chloroform. These were tightly closed and kept at −20° C. pending assay.

The total lipids were separated by thin-layer chromatography on Silica G plates using petroleum ether/diethyl ether/acetic acid (80:20:1, v/v/v) and were visualized by either fluoroscein or iodine vapor. Free and esterified cholesterol bands were localized from their Rf values as determined using pure standards. They were scraped, eluted with hexane and analyzed by gas chromatography using a Shimadzu Model 9A gas chromatograph equipped with either an Ultra-1 capillary column (50 m×0.2 mm×0.33 µm, Hewlett-Packard, Avondale, Pa.) or SP-2330 fused silica capillary column (15 m×0.25 mm×0.20 mm, Supelco, Bellefonte, Pa.) with 5-alpha-cholestane as the internal standard (Serdary Research Laboratory, London, Ontario). Mass assays were quantified by integration of the areas under the peaks with a Hewlett-Packard 3390A integrator. The identity of the cholesterol peak was confirmed using pure cholesterol standard. Cholesterol ester was determined by elution from the thin-layer chromatography plate followed by extraction with ethanol, hydrolysis of the eluted band in 33% KOH and back extraction of the free cholesterol with hexane and analysis by gas chromatography.

Figure 2:
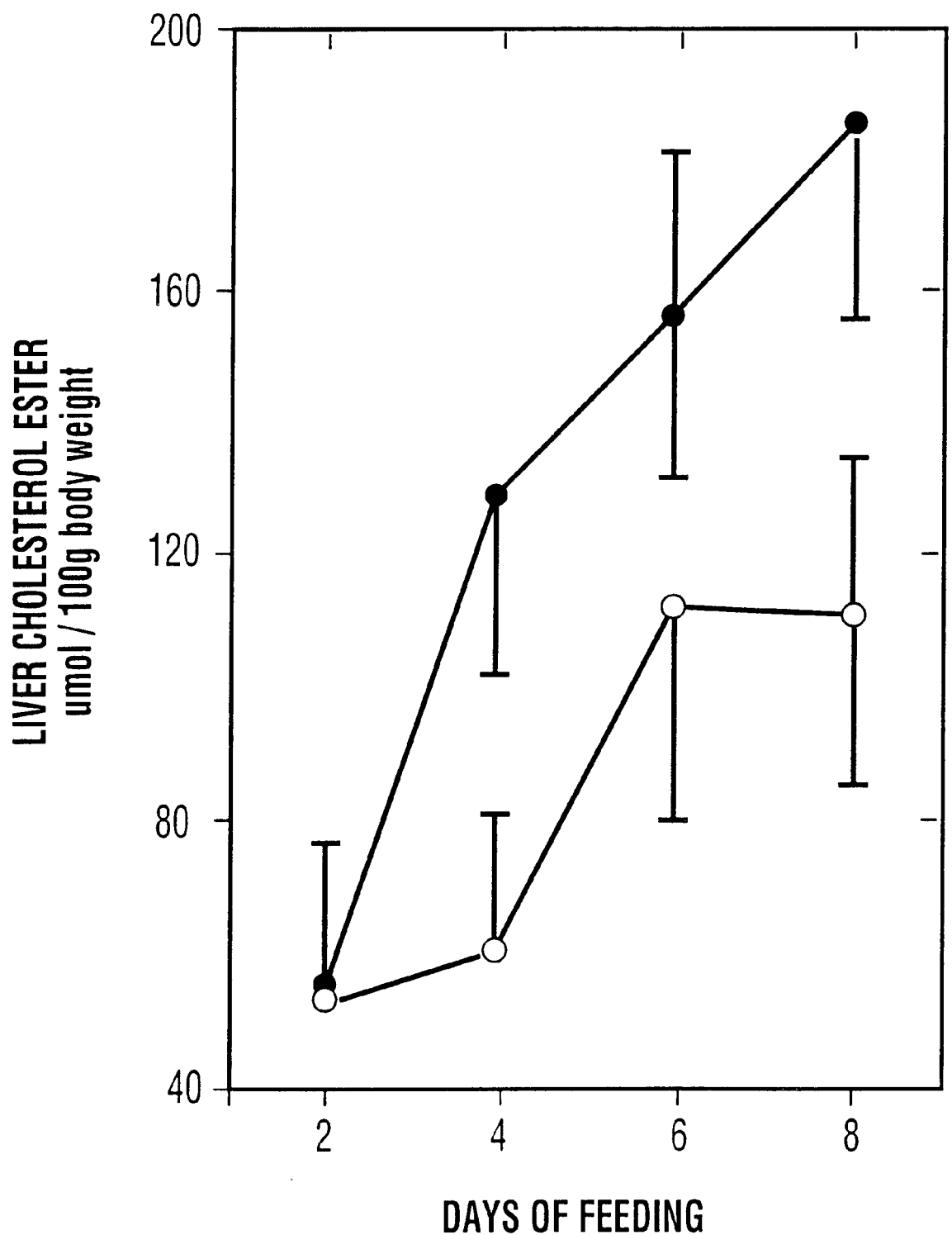
FIG. 2 graphically illustrates the difference in the amount of cholesterol ester that accumulates in the livers of rats fed cholesterol alone and rats fed cholesterol combined with an oxysterol composition.

The results are summarized in FIG. 2. When a diet supplemented with cholesterol was fed to rats for 8 days, the liver content of cholesterol ester increased steeply after 2 and 4 days. The rate of increase declined after the $4^{th}$ day but still showed a progressive rise between the $6^{th}$ and the $8^{th}$ day of feeding. Oxysterol supplemented diet reduced the liver cholesterol ester accumulation at 4, 6 and 8 days, as compared to the group fed high cholesterol alone for the same period of time. The liver levels of free cholesterol, triglyceride and phospholipids were not changed by either diet. The animals remained healthy, consumed equal amounts of food and gained weight identically in all groups, regardless of the diet used.

Figure 3:
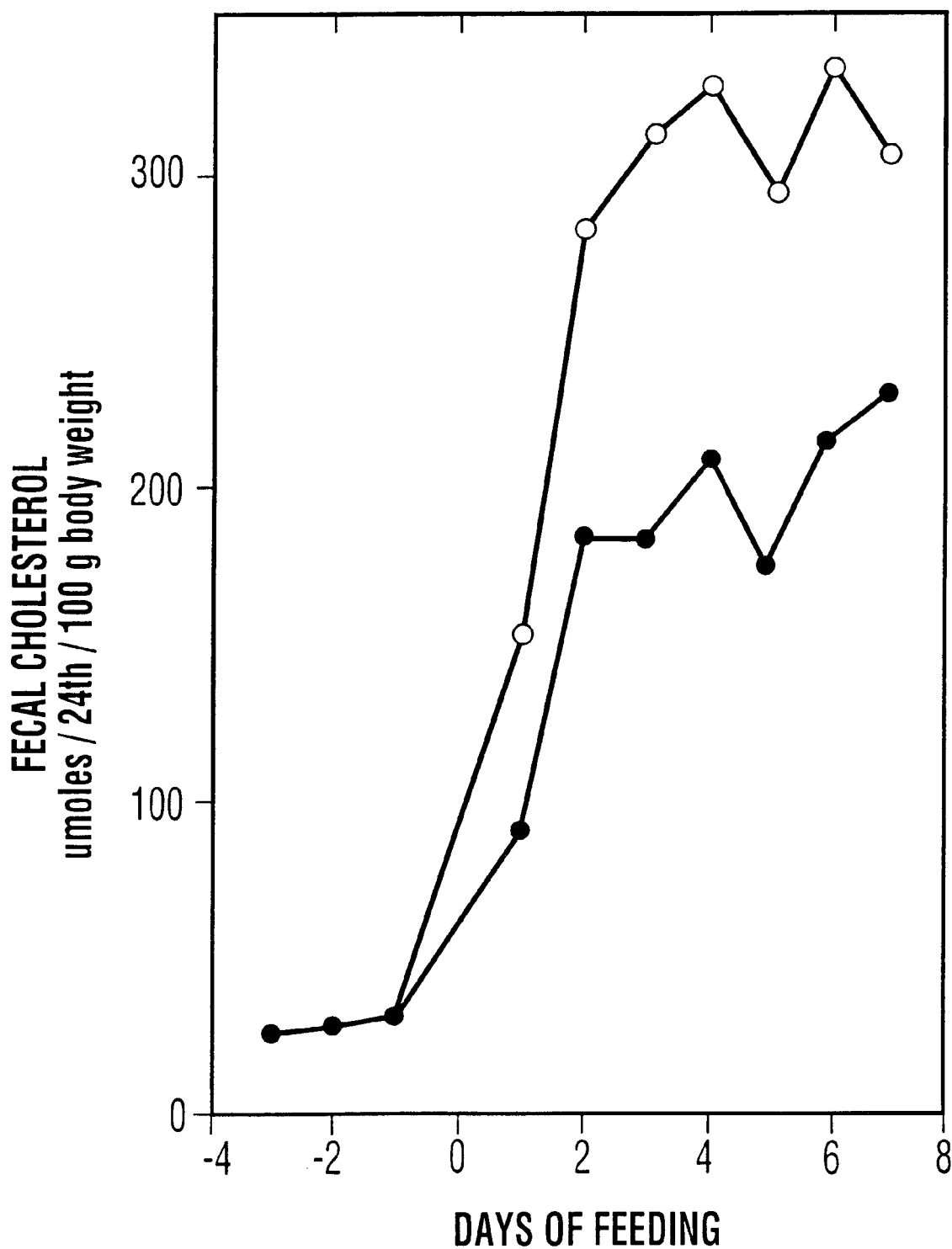
FIG. 3 graphically illustrates the difference in fecal cholesterol of the two groups of rats identified in FIG. 2.

As shown in FIG. 3, cholesterol excretion in feces was undetectable in the rats fed cholesterol-free diet. It rose steeply in the first 2 days of cholesterol feeding and then plateaued until the experiment was terminated after 7 days. The mean pooled daily fecal cholesterol excretion was 191+/−29 µmol/100 g body weight in rats fed a pure cholesterol diet. For those fed cholesterol and oxysterols, the daily fecal cholesterol loss was 307+/−19 µmol/100 g body weight (p<0.01). Daily cholesterol intake for both groups of rats was 480+/−56 µmol/100 g body weight. Thus, as can be seen, the oxysterol composition dramatically decreases the absorption of dietary cholesterol.

Example 3
In vivo Studies of Intragastric Cholesterol Absorption

In this experiment, the effect of oxysterols on intestinal absorption of cholesterol and transport to liver was estimated by intragastric injection of (4–14C)cholesterol in the presence and absence of oxysterols. The method generally described by Kelley and Tsai (Journal of Nutrition (1978), vol 108, page 630) was used.

Rats were maintained on the cholesterol-free basal diet as described in Example 2 for 5 days. On the 6$^{th}$ day, the food dishes were removed at 0700 and between 10.45–11.45 am, the rats were anesthetized briefly with diethyl either. An intragastric tube was inserted into each rat and then 1 ml of a cholesterol emulsion or 1 ml of an oxysterol emulsion was administered into the stomach via the tube.

The cholesterol emulsion was prepared by adding cholesterol in an amount of from 10 to 100 mg per ml to a mixture of corn oil and absolute ethanol (7:1, v/v). In some experiments oleic acid plus corn oil (2:8, v/v) was used. To this mixture was then added (4–14C)cholesterol (obtained from New England Nuclear, Boston Mass.) dissolved in absolute ethanol (0.5 µCi/ml emulsion). The final composition was:

| cholesterol | 10–100 mg per ml |
|---|---|
| (4-14C) cholesterol | 0.5 uCl/.ml |
| oleic acid* | 0.2 ml/ml |
| ethanol | 0.1 ml/ml |
| corn oil | to 1.0 ml/ml |

(*used only in some experiments)

The emulsion was homogenized in a Potter-Elvejhem homogenizer, sonicated and held at 35° C. prior to the experiment.

The oxysterol emulsion contained pure cholesterol as set out above plus 50 mg of oxysterols (obtained as described in Example 1 from a crude mixture) per 1.0 ml in corn oil. (4–14C) cholesterol dissolved in absolute ethanol was added (0.5 µCi/ml). The emulsions were homogenized with a Potter-Elvejhem homogenizer as described for the cholesterol emulsion.

The rats were returned to their cages following administration of the selected emulsion, and at 4 and 6 hours, groups of rats were re-anesthetized and exsanguianted by aortic puncture. Liver and blood lipids were separated on Silica G plates as described in Example 2. Free cholesterol and cholesterol ester bands were scraped directly into vials and counted in 10 ml of Atomlight (Dupont) in a Beckman LS 7500 scintillation counter. All radioactivity measurements were automatically quench-corrected by the channels ratio method.

The net transport of administered cholesterol to liver (µmol/h) was calculated using the total disintegrations per minute (DPM) recovered in liver lipid and the specific radioactivity of the administered cholesterol, by the following equation:

$$\text{cholesterol } (\mu\text{mol/h}) \text{ transported to liver} = \frac{\text{liver DPM}}{\text{hours}} \times \frac{1}{\text{S.A. (DPM/}\mu\text{mol)}}$$

Figure 4:
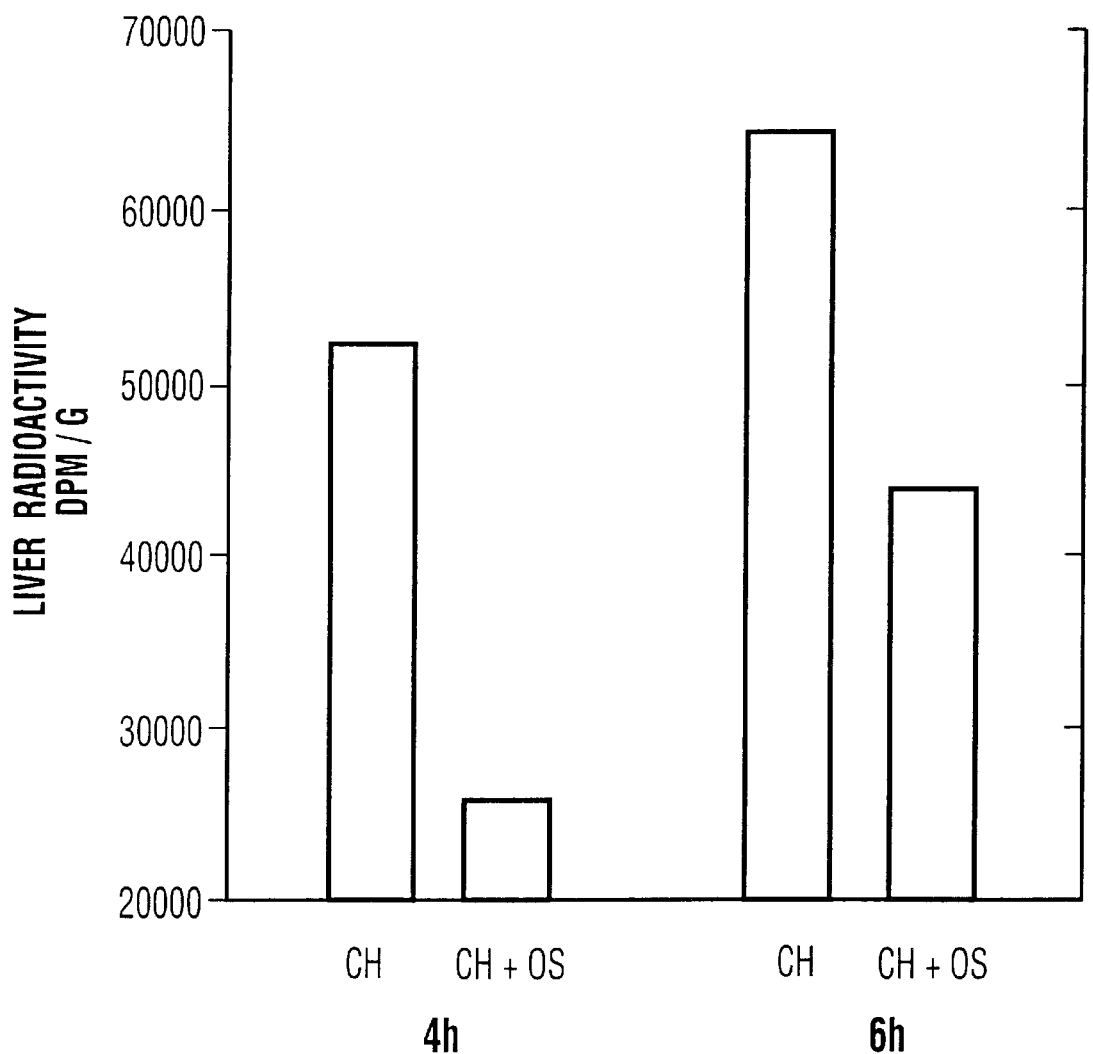
FIG. 4 is a bar graph illustrating the effect of oxysterols on uptake of {14C}cholesterol.

Addition of a mixture of 50 mg of oxysterols containing 260 µmol cholesterol decreased the recovery of radioactivity in liver after 4 and 6 hr by approximately 50% as compared to the control group into which was injected cholesterol alone (FIG. 4). The extent of the decrease was similar at both time intervals. An identical pattern was observed in blood radioactivity levels.

Example 4
Dose-Related Study

An experiment similar to that described in Example 3 was conducted to determine the relation of activity to dose of oxysterols. In this experiment the different groups of rats were intragastrically administered different doses of oxysterols as follows: Group I, 0 mg oxysterols; Group II, 12.5 mg oxysterols; Group III, 25 mg oxysterols; and Group IV, 50 mg oxysterols. The oxysterols were administered in the form of an oxysterol emulsion prepared as described in Example 3 with the given amount of oxysterols (crude) and 50 mg of pure cholesterol.

Oxysterols inhibited cholesterol absorption in a dose-dependent manner as observed in blood and liver radioactivities after 4 hr following administration of a single intragastric dose of cholesterol (50 mg) plus various amounts of oxysterols (12.5, 25 and 50 mg) as shown in the table below. Reduction of cholesterol absorption was present at each dose of oxysterol, but was most potent at the highest dose of oxysterols.

| Group | Cholesterol (mg) | Oxysterol (mg) | Liver Radioactivity (DPM) |
|---|---|---|---|
| I | 50 | 0 | 39,168 +/− 15084 |
| II | 50 | 12.5 | 24,308 +/− 6405 |
| III | 50 | 25 | 24,300 +/− 7653 |
| IV | 50 | 50 | 16,152 +/− 3496 |

I claim:

1. A composition that reduces the absorption of dietary cholesterol into the body of a human, said composition comprising a therapeutically effective amount of from about 0.1–1 per day of at least one pharmaceutically acceptable oxysterol which is effective to reduce the absorption of dietary cholesterol and at least one carrier.

2. A composition as defined in claim 1, in which the at least one oxysterol is more polar than cholesterol.

3. A composition as defined in claim 2, which comprises at least one oxysterol selected from the group consisting of 20-hydroxy cholesterol, 7-hydroxy cholesterol and 5,6-cholestan epoxide.

4. A composition as defined in claim 1, in capsule form.

5. A composition as defined in claim 1, in the form of an oily preparation.

6. A composition as defined in claim 1, which comprises at least 7-hydroxy cholesterol.

7. A method of reducing dietary cholesterol absorption by a mammal comprising the step of administering to said mammal a therapeutically effective amount of a pharmaceutically acceptable composition comprising at least one oxysterol which is effective to reduce dietary cholesterol absorption.

8. A method as defined in claim 7, wherein said oxysterol composition comprises at least one oxysterol which is more polar than cholesterol in combination with at least one carrier.

9. A method as defined in claim 8, wherein said oxysterol composition comprises at least one oxysterol selected from the group consisting of 20-hydroxy cholesterol, 7-hydroxy cholesterol and 5,6-cholestan epoxide.

10. A method as defined in claim 7, wherein said therapeutically effective amount is in the range of 0.1–1 gram per day.

11. A method as defined in claim 10, wherein said composition is administered in capsule form.

12. A method as defined in claim 10, wherein said composition is administered as an oily preparation.

13. A method as defined in claim 12, wherein the oily preparation is administered in combination with a food.

14. A method as defined in claim 7, wherein said oxysterol composition comprises at least 7-hydroxy cholesterol.

15. An orally administrable dietary supplement effective to reduce the absorption of dietary cholesterol in a human, said supplement comprising at least one carrier and a pharmaceutically acceptable combination of one or more therapeutically effective oxysterols in an amount of 0.1–1 gram per day.

16. A dietary supplement as defined in claim 15, comprising at least one oxysterol which is more polar than cholesterol and is therapeutically effective to reduce absorption of dietary cholesterol in a mammal.

17. A dietary supplement as defined in claim 16, wherein at least one of said oxysterols is selected from the group consisting of 20-hydroxy cholesterol, 7-hydroxy cholesterol and 5,6-cholestan epoxide.

18. A dietary supplement as defined in claim 15, which is in the form of an oily preparation.

19. A dietary supplement as defined in claim 15, comprising at least 7-hydroxy cholesterol.

20. An article of manufacture comprising packaging material and an orally administrable pharmaceutical composition contained within said packaging material, wherein said pharmaceutical composition is therapeutically effective to reduce absorption of dietary cholesterol in a human, and wherein the packaging material comprises a label which indicates that the composition can be used in an amount of about 0.1–1 gram per day to reduce absorption of dietary cholesterol in a mammal, said composition comprising a pharmaceutically acceptable combination of one or more oxysterols which are therapeutically effective to reduce absorption of dietary cholesterol and at least one carrier.

21. An article of manufacture as defined in claim 20, wherein said composition comprises at least one therapeutically effective oxysterol which is more polar than cholesterol.

22. An article of manufacture as defined in claim 21, wherein said composition comprises at least one oxysterol is selected from the group consisting of 20-hydroxy cholesterol, 7-hydroxy cholesterol and 5,6-cholestan epoxide.

23. An article of manufacture as defined in claim 20, wherein said composition is in capsule form or in the form of an oily preparation.

24. An article of manufacture as defined in claim 20, comprising at least 7-hydroxy cholesterol.

* * * * *